(12) United States Patent
Toth et al.

(10) Patent No.: US 8,199,874 B2
(45) Date of Patent: Jun. 12, 2012

(54) SYSTEM AND METHOD OF MITIGATING LOW SIGNAL DATA FOR DUAL ENERGY CT

(75) Inventors: Thomas L. Toth, Brookfield, WI (US); Jiang Hsieh, Brookfield, WI (US); Naveen Chandra, Kenosha, WI (US); Xiaoye Wu, Rexford, NY (US)

(73) Assignee: General Electric Company, Schenectady, NY (US)

( * ) Notice: Subject to any disclaimer, the term of this patent is extended or adjusted under 35 U.S.C. 154(b) by 417 days.

(21) Appl. No.: 12/635,901

(22) Filed: Dec. 11, 2009

(65) Prior Publication Data

US 2011/0142312 A1    Jun. 16, 2011

(51) Int. Cl.
*A61B 6/00* (2006.01)
*H05G 1/64* (2006.01)

(52) U.S. Cl. .... 378/16; 378/98.9; 378/98.11; 378/98.12
(58) Field of Classification Search ............... 378/4, 16, 378/98.9, 98.11, 98.12
See application file for complete search history.

(56) References Cited

U.S. PATENT DOCUMENTS

| | | | |
|---|---|---|---|
| 6,614,874 B2 * | 9/2003 | Avinash ..................... 378/62 |
| 6,661,873 B2 * | 12/2003 | Jabri et al. ................ 378/98.11 |
| 6,678,350 B2 * | 1/2004 | Dolazza et al. ............. 378/98.9 |
| 7,054,407 B1 | 5/2006 | Li et al. | |
| 7,236,559 B2 * | 6/2007 | Jha et al. ........................ 378/5 |
| 2006/0109951 A1 | 5/2006 | Popescu | |
| 2009/0097611 A1 | 4/2009 | Nishide et al. | |
| 2009/0180585 A1 | 7/2009 | Fujimoto et al. | |
| 2011/0142194 A1 * | 6/2011 | Chandra et al. ............... 378/16 |

FOREIGN PATENT DOCUMENTS

| | | |
|---|---|---|
| EP | 1734405 A2 | 12/2006 |
| EP | 1980207 A1 | 10/2008 |

OTHER PUBLICATIONS

Search Report from corresponding EP Application No. 11161801.3 dated Jul. 27, 2011.

* cited by examiner

*Primary Examiner* — Edward Glick
*Assistant Examiner* — Alexander H Taningco
(74) *Attorney, Agent, or Firm* — Ziolkowski Patent Solutions Group, SC

(57) ABSTRACT

A CT system includes a rotatable gantry having an opening for receiving an object to be scanned, and a controller configured to obtain kVp projection data at a first kVp, obtain kVp projection data at a second kVp, extract data from the kVp projection data obtained at the second kVp, add the extracted data to the kVp projection data obtained at the first kVp to generate mitigated projection data at the first kVp, and generate an image using the mitigated projection data at the first kVp and using the projection data obtained at the second kVp.

27 Claims, 8 Drawing Sheets

SYSTEM AND METHOD OF MITIGATING LOW SIGNAL DATA FOR DUAL ENERGY CT

BACKGROUND OF THE INVENTION

Embodiments of the present invention relate generally to diagnostic imaging and, more particularly, to an apparatus and method of acquiring imaging data at more than one energy range using a multi-energy imaging source.

Typically, in computed tomography (CT) imaging systems, an x-ray source emits a fan-shaped or cone-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis, which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom. Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

A CT imaging system may include an energy sensitive (ES), multi-energy (ME), and/or dual-energy (DE) CT imaging system that may be referred to as an ESCT, MECT, and/or DECT imaging system, in order to acquire data for material decomposition or effective Z or monochromatic image estimation. ESCT/MECT/DECT provides energy discrimination. For example, in the absence of object scatter, the system derives the material attenuation at a different energy based on the signal from two relative regions of photon energy from the spectrum: the low-energy and the high-energy portions of the incident x-ray spectrum. In a given energy region relevant to medical CT, two physical processes dominate the x-ray attenuation: (1) Compton scatter and the (2) photoelectric effect. These two processes are sensitive to the photon energy and hence each of the atomic elements has a unique energy sensitive attenuation signature. Therefore, the detected signals from two energy regions provide sufficient information to resolve the energy dependence of the material being imaged. Furthermore, detected signals from the two energy regions provide sufficient information to determine the materials attenuation coefficients in terms of Compton scatter and photoelectric effect. Alternatively, the material attenuation may be expressed as the relative composition of an object composed of two hypothetical materials, or the density and effective atomic number with the scanned object. As understood in the art, using a mathematical change of basis, energy sensitive attenuation can be expressed in terms of two base materials, densities, effective Z number, or as two monochromatic representations having different keV.

Such systems may use a direct conversion detector material in lieu of a scintillator. The ESCT, MECT, and/or DECT imaging system in an example is configured to be responsive to different x-ray spectra. Energy sensitive detectors may be used such that each x-ray photon reaching the detector is recorded with its photon energy. One technique to acquire projection data for material decomposition includes using energy sensitive detectors, such as a CZT or other direct conversion material having electronically pixelated structures or anodes attached thereto. However, such systems typically include additional cost and complexity of operation in order separate and distinguish energy content of each received x-ray photon.

In an alternative, a conventional scintillator-based third-generation CT system may be used to provide energy sensitive measurements. Such systems may acquire projections sequentially at different peak kilovoltage (kVp) operating levels of the x-ray tube, which changes the peak and spectrum of energy of the incident photons comprising the emitted x-ray beams. A principle objective of scanning with two distinctive energy spectra is to obtain diagnostic CT images that enhance information (contrast separation, material specificity, etc.) within the image by utilizing two scans at different polychromatic energy states.

One technique has been proposed to achieve energy sensitive scanning including acquiring two scans at, for instance, 80 kVp and 140 kVp. The two scans may be obtained (1) back-to-back sequentially in time where the scans require two rotations of the gantry around the subject that may be hundreds of milliseconds to seconds apart, (2) interleaved as a function of the rotation angle requiring one rotation around the subject, or (3) using a two tube/two detector system with the tubes/detectors mounted ~90 degrees apart, as examples.

High frequency, low capacitance generators have made it possible to switch the kVp potential of the high frequency electromagnetic energy projection source on alternating views and interleave datasets. As a result, data for two energy sensitive scans may be obtained in a temporally interleaved fashion rather than with separate scans made several seconds apart or with a two tube/two detector system. In order to improve contrast and reduce or eliminate beam hardening artifacts, it is desirable to increase energy separation between high and low kVp scans. Energy separation may be increased by increasing energy in high kVp scans. However, high kVp scans may be limited due to system stability at high voltage.

Alternatively, energy separation may be increased by decreasing energy in low kVp scans. However, x-ray attenuation may occur for low kVp projections to the extent that system noise may swamp a received signal, and x-ray attenuation typically increases as the size of the imaging object increases. As may be experienced in conventional single kVp imaging, imaging of some objects at, for instance, up to 120 kVp can cause projection data to be contaminated as detected signals become so weak that they are swamped out by other interfering signals such as electronic system noise and scattered x-ray noise. Thus, in conventional CT it is possible to intervene with a low signal mitigation algorithm to avoid low signal streaking artifacts in images. Such algorithms may be applied to one or both sets of scan data in a dual energy application, as well.

However, as understood in the art, low signal mitigation algorithms are typically data smoothing filters that operate along a detector channel, detector row, and/or view dimensions. And, although known algorithms may reduce streaking, they also may reduce high spatial frequency content of data samples, and therefore resolution, in resulting images.

Thus, there is a need for low signal mitigation in potentially a large percentage of dual or multi-energy exams that are conducted.

Therefore, it would be desirable to design a mitigation scheme for low kVp imaging that does not compromise high spatial frequency content thereof.

BRIEF DESCRIPTION OF THE INVENTION

Embodiments of the invention are directed to a method and apparatus for mitigating low signal imaging data that overcomes the aforementioned drawbacks.

According to an aspect of the invention, a CT system includes a rotatable gantry having an opening for receiving an object to be scanned, and a controller configured to obtain kVp projection data at a first kVp, obtain kVp projection data at a second kVp, extract data from the kVp projection data obtained at the second kVp, add the extracted data to the kVp projection data obtained at the first kVp to generate mitigated projection data at the first kVp, and generate an image using the mitigated projection data at the first kVp and using the projection data obtained at the second kVp.

According to another aspect of the invention, a method of CT imaging includes obtaining one or more first kVp projection datasets, obtaining a plurality of second kVp projection datasets, extracting information from the plurality of second kVp projection datasets, adding the extracted information to one of the first kVp projection datasets to generate a corrected first kVp projection dataset, and generating an image using at least the corrected first kVp projection dataset.

According to yet another aspect of the invention, a computer readable storage medium having stored thereon a computer program comprising instructions which when executed by a computer cause the computer to obtain first kVp view data, obtain second kVp view data, extract high frequency data from the second kVp view data, adjust the first kVp view data using the extracted high frequency data to generate adjusted first kVp view data, and generate an image using the adjusted first kVp view data.

These and other advantages and features will be more readily understood from the following detailed description of preferred embodiments of the invention that is provided in connection with the accompanying drawings.

DETAILED DESCRIPTION

Diagnostics devices comprise x-ray systems, magnetic resonance (MR) systems, ultrasound systems, computed tomography (CT) systems, positron emission tomography (PET) systems, ultrasound, nuclear medicine, and other types of imaging systems. Applications of x-ray sources comprise imaging, medical, security, and industrial inspection applications. However, it will be appreciated by those skilled in the art that an implementation is applicable for use with single-slice or other multi-slice configurations. Moreover, an implementation is employable for the detection and conversion of x-rays. However, one skilled in the art will further appreciate that an implementation is employable for the detection and conversion of other high frequency electromagnetic energy. An implementation is employable with a "third generation" CT scanner and/or other CT systems.

The operating environment of the present invention is described with respect to a sixty-four-slice computed tomography (CT) system. However, it will be appreciated by those skilled in the art that the present invention is equally applicable for use with other multi-slice configurations, and with systems having a capability of shifting, or "wobbling" the focal spot during operation. Moreover, the present invention will be described with respect to the detection and conversion of x-rays. However, one skilled in the art will further appreciate that the present invention is equally applicable for the detection and conversion of other high frequency electromagnetic energy. The present invention will be described with respect to a "third generation" CT scanner, but is equally applicable with other CT systems.

A dual energy CT system and method is disclosed. Embodiments of the invention support the acquisition of both anatomical detail as well as tissue characterization information for medical CT, and for components within luggage. Energy discriminatory information or data may be used to reduce the effects of beam hardening and the like. The system supports the acquisition of tissue discriminatory data and therefore provides diagnostic information that is indicative of disease or other pathologies. This detector can also be used to detect, measure, and characterize materials that may be injected into the subject such as contrast agents and other specialized materials by the use of optimal energy weighting to boost the contrast of iodine and calcium (and other high atomic or materials). Contrast agents can, for example, include iodine that is injected into the blood stream for better visualization. For baggage scanning, the effective atomic number generated from energy sensitive CT principles allows reduction in image artifacts, such as beam hardening, as well as provides addition discriminatory information for false alarm reduction.

Figure 1:
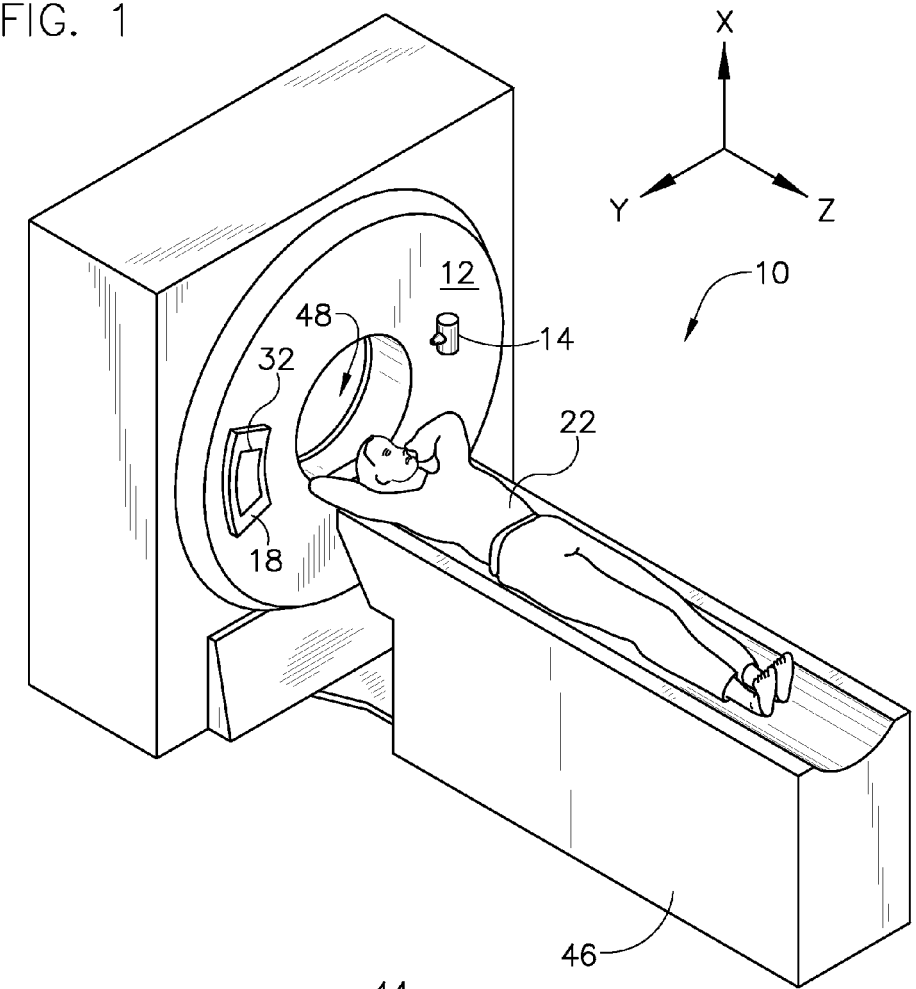
FIG. 1 is a pictorial view of a CT imaging system.
Figure 2:
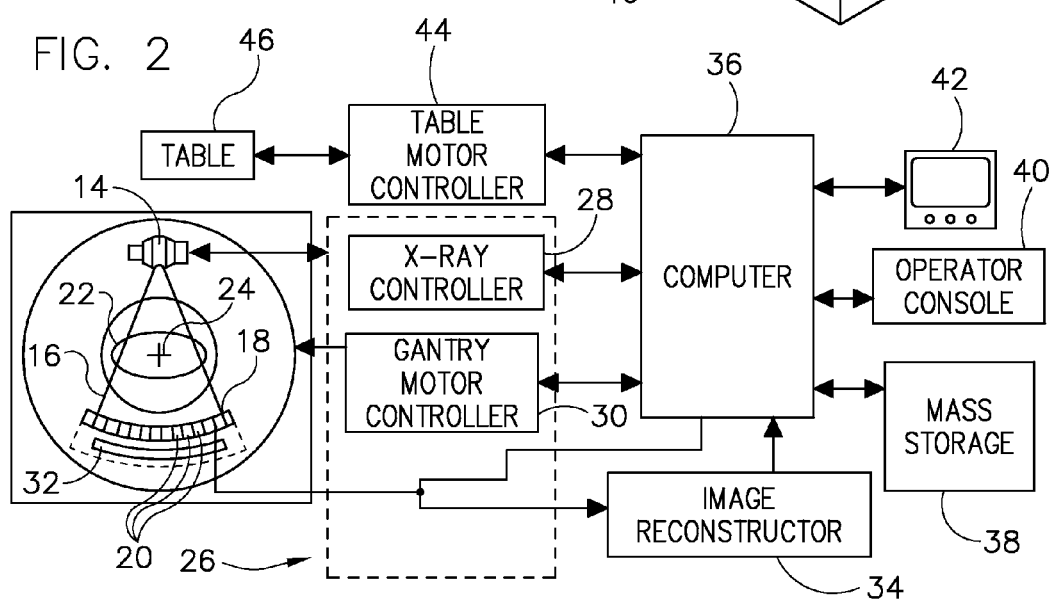
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector assembly 18 that includes a collimator on the opposite side of the gantry 12. In embodiments of the invention, x-ray source 14 includes either a stationary target or a rotating target. Detector assembly 18 is formed by a plurality of detectors 20 and data acquisition systems (DAS) 32. The plurality of detectors 20 sense the projected x-rays that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 and generator 29 that provides power and timing signals to x-ray source 14 and a gantry motor controller 30 that controls the rotational speed and position of gantry 12. An image reconstructor 34 receives sampled and digitized x-ray data from DAS 32 and performs high speed reconstruction. The reconstructed image and the embodiments described herein are applied as an input to a computer 36 which stores the image in a mass storage device 38, which may include computer RAM, discs, and the like.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

System 10 may be operated in either monopolar or bipolar modes. In monopolar operation, either the anode is grounded and a negative potential is applied to the cathode, or the cathode is grounded and a positive potential is applied to the anode. Conversely, in bipolar operation, an applied potential is split between the anode and the cathode. In either case, monopolar or bipolar, a potential is applied between the anode and cathode, and electrons emitting from the cathode are caused to accelerate, via the potential, toward the anode. When, for instance, a −140 kV voltage differential is maintained between the cathode and the anode and the tube is a bipolar design, the cathode may be maintained at, for instance, −70 kV, and the anode may be maintained at +70 kV. In contrast, for a monopolar design having likewise a −140 kV standoff between the cathode and the anode, the cathode accordingly is maintained at this higher potential of −140 kV while the anode is grounded and thus maintained at approximately 0 kV. Accordingly, the anode is operated having a net 140 kV difference with the cathode within the tube.

Figure 3:
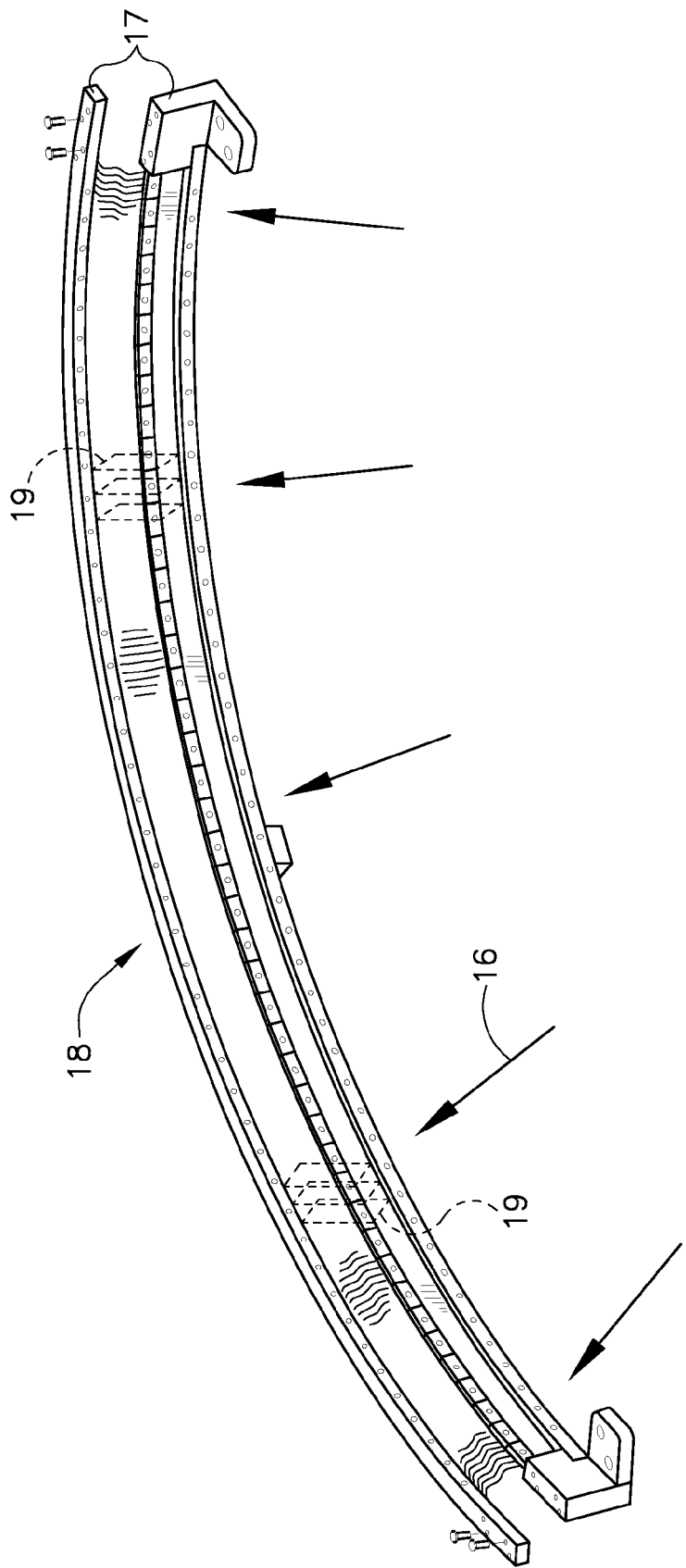
FIG. 3 is a perspective view of one embodiment of a CT system detector array.

As shown in FIG. 3, detector assembly 18 includes rails 17 having collimating blades or plates 19 placed therebetween. Plates 19 are positioned to collimate x-rays 16 before such beams impinge upon, for instance, detector 20 of FIG. 4 positioned on detector assembly 18. In one embodiment, detector assembly 18 includes 57 detectors 20, such as will be illustrated, each detector 20 having an array size of 64×16 of pixel elements 50. As a result, detector assembly 18 has 64 rows and 912 columns (16×57 detectors) which allows 64 simultaneous slices of data to be collected with each rotation of gantry 12.

Figure 4:
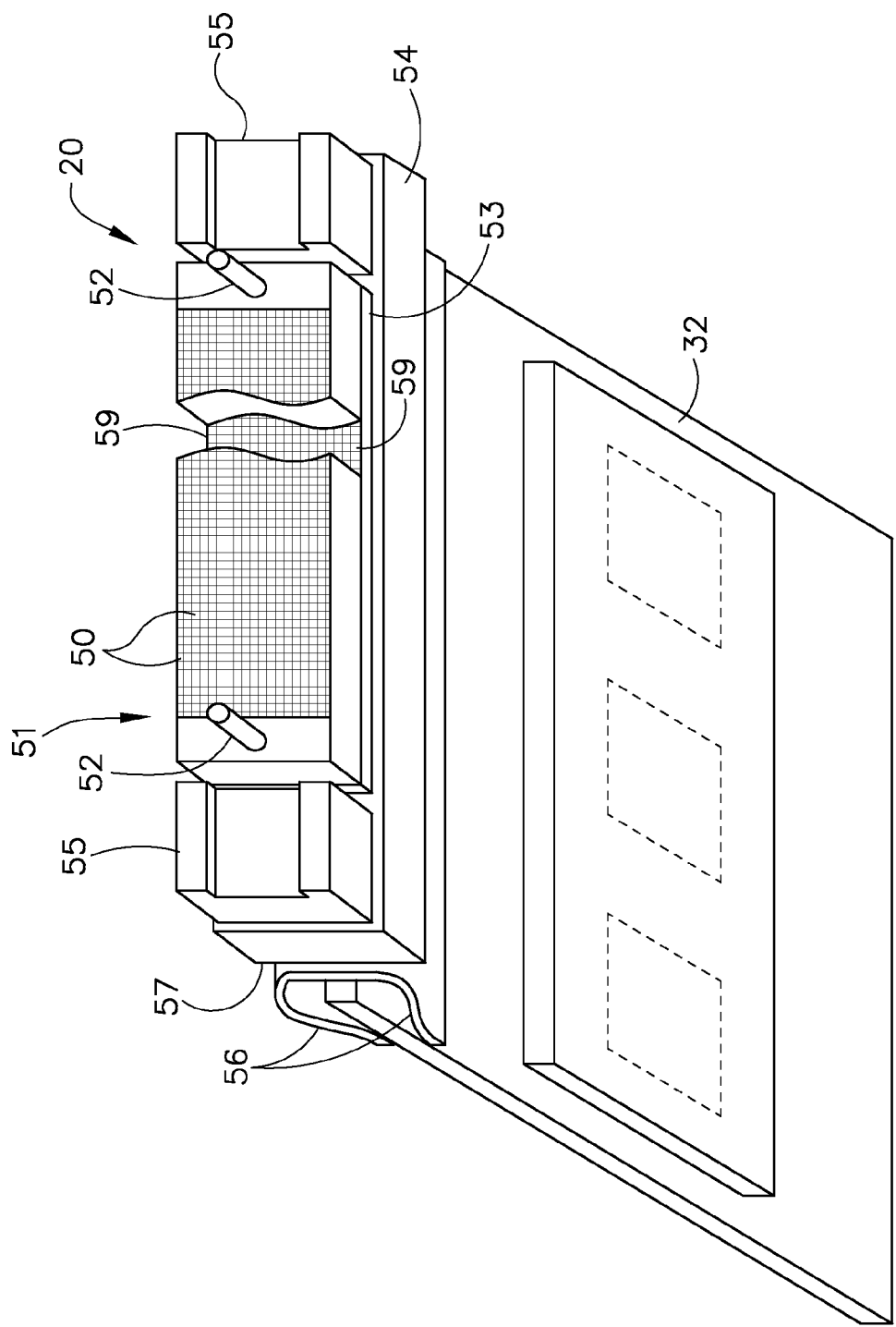
FIG. 4 is a perspective view of one embodiment of a detector.

Referring to FIG. 4, detector 20 includes DAS 32, with each detector 20 including a number of detector elements 50 arranged in pack 51. Detectors 20 include pins 52 positioned within pack 51 relative to detector elements 50. Pack 51 is positioned on a backlit diode array 53 having a plurality of diodes 59. Backlit diode array 53 is in turn positioned on multi-layer substrate 54. Spacers 55 are positioned on multi-layer substrate 54. Detector elements 50 are optically coupled to backlit diode array 53, and backlit diode array 53 is in turn electrically coupled to multi-layer substrate 54. Flex circuits 56 are attached to face 57 of multi-layer substrate 54 and to DAS 32. Detectors 20 are positioned within detector assembly 18 by use of pins 52.

In the operation of one embodiment, x-rays impinging within detector elements 50 generate photons which traverse pack 51, thereby generating an analog signal which is detected on a diode within backlit diode array 53. The analog signal generated is carried through multi-layer substrate 54, through flex circuits 56, to DAS 32 wherein the analog signal is converted to a digital signal.

The following discussion refers to an embodiment of the invention that includes high and low kVp projection datasets from a single energy source having a single detector and a single controller. However, it is to be understood that the invention is equally applicable to a broad range of systems that include but are not limited to having two more sources and two or more detectors. In such systems, a single controller may be used for controlling the sources and detectors, or multiple controllers may be used.

Further, the following discussion refers to obtaining low kVp and high kVp projection data, and correcting the low kVp projection data using the high kVp projection data, as will be further described. However, it is to be understood that the invention is generally applicable to correction of data obtained at one kVp by using data obtained at another kVp. For instance, in the following discussion it is assumed that the low kVp data includes a higher level of noise (or worse statistics), that can lead to image artifacts, than the high kVp data, and thus the high kVp data is used to correct the low kVp data. But, in instances where lower noise or better statistics are obtained in the low kVp projection data as compared to the obtained high kVp projection data, this invention is likewise applicable thereto, and a high frequency component of, or statistics from, the low kVp projection data, in this example, could equally be used to correct for high noise and/or poor statistics in the high kVp projection data.

Figure 5:
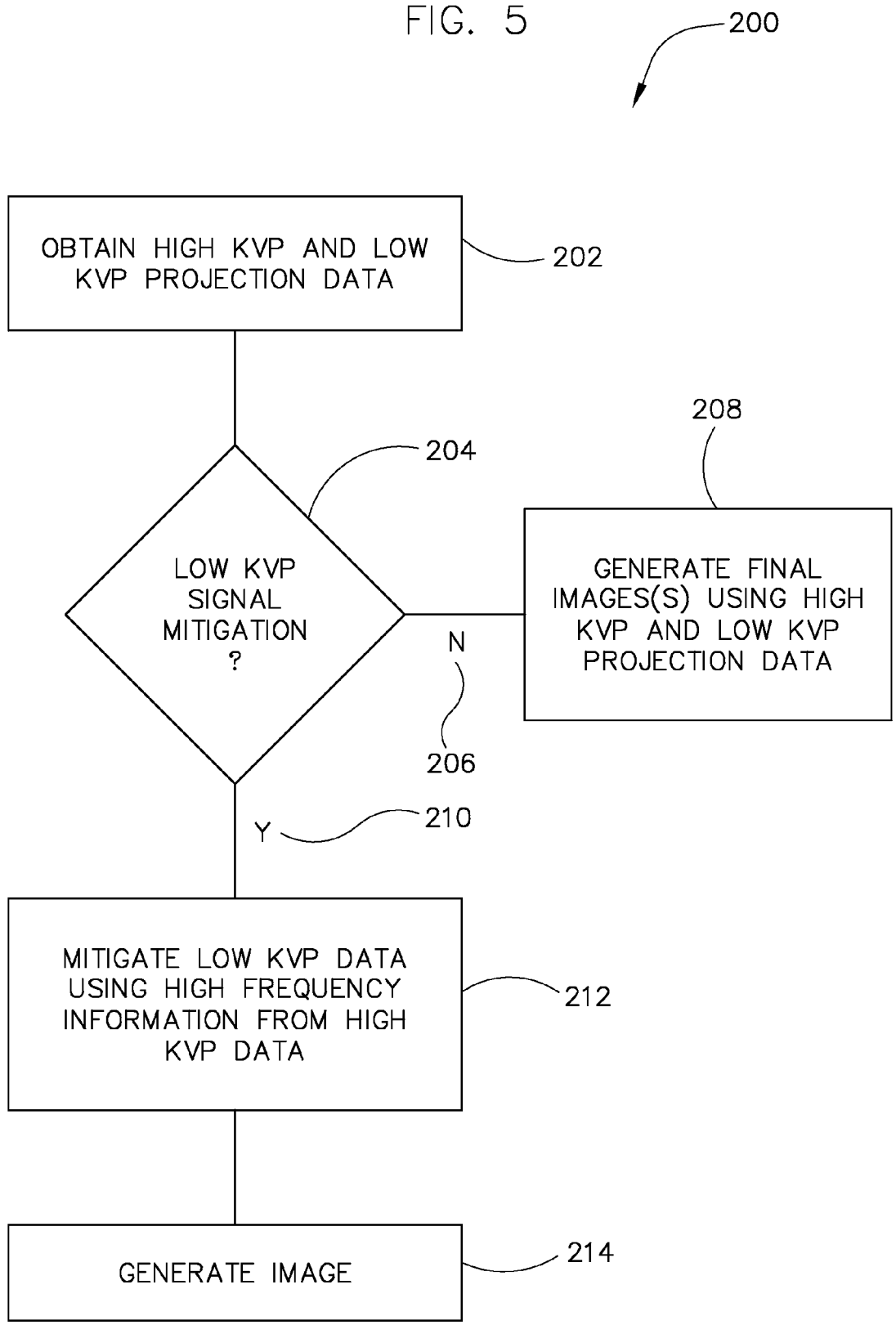
FIG. 5 is a flowchart for adjusting low kVp data according to an embodiment of the invention.

Referring to FIG. 5, a technique 200 for acquiring and mitigating low kVp CT imaging data is shown. Technique 200 includes acquiring high and low kVp projection data or datasets at step 202 using, for instance, generator 29 of FIG. 2 to energize source 14, and determining at step 204 whether to apply a low kVp signal mitigation or correction step, according to embodiments of the invention. The determination at step 204 may be objectively based on a low signal threshold (LST) value, system characteristics, image acquisition settings, and the like. Alternatively, the determination at step 204 may be subjectively based on a user observation when, for instance, streaking or other artifacts are observed in final images.

If no mitigation or correction step is to be applied 206, then final images are generated at step 208 using the high and kVp projection data acquired at step 202. However, if mitigation or correction is to be applied 210, then high frequency data from high kVp projection data is used to mitigate low kVp projection data at step 212, as will be further illustrated in FIG. 6. A dual-energy image is generated at step 214 using the acquired high kVp projection data and the adjusted low kVp projection data, according to known methods for dual-energy image reconstruction.

Figure 6:
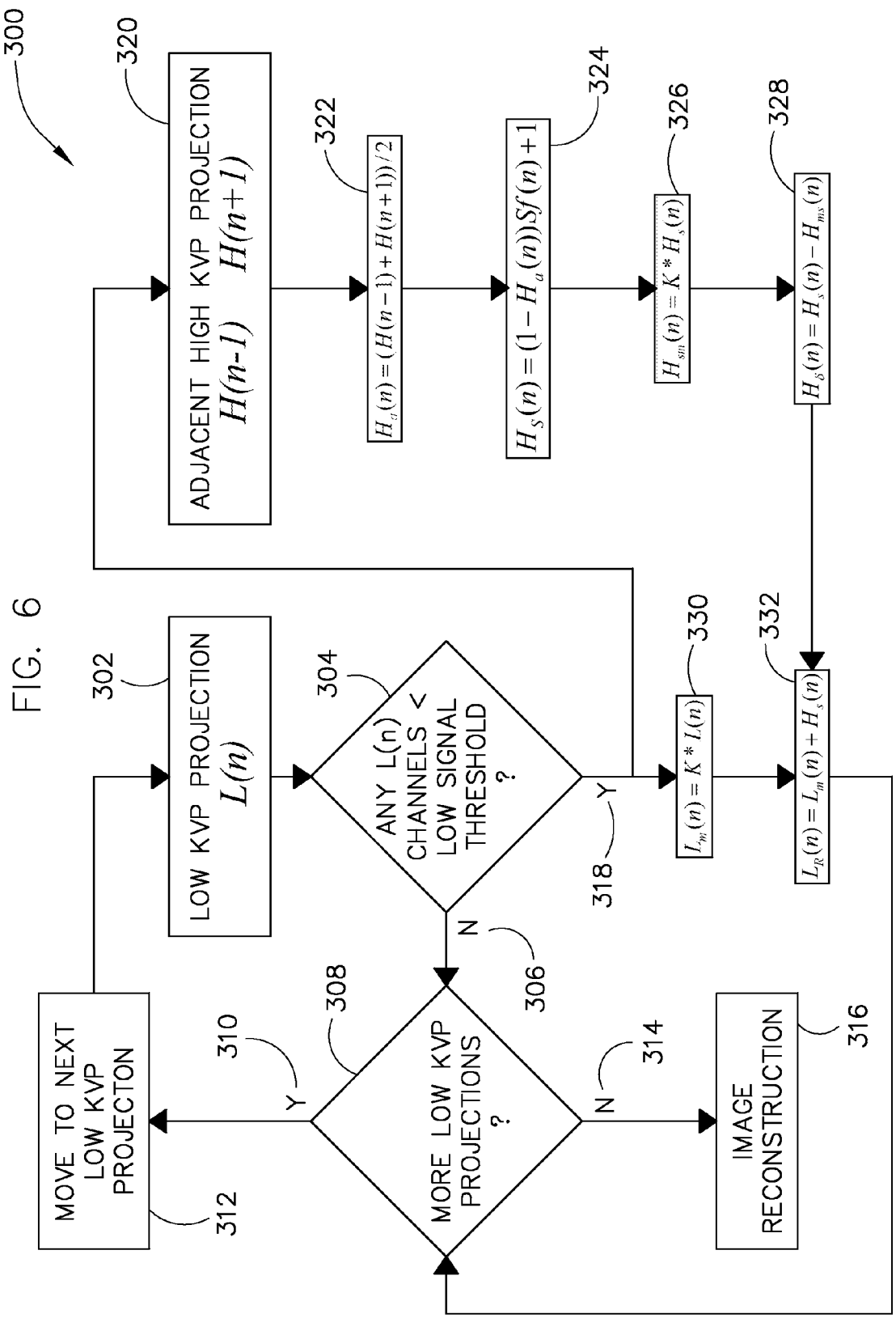
FIG. 6 is a flowchart for adjusting low kVp data according to an embodiment of the invention.

Once it has been determined to mitigate low kVp data at step 210 of FIG. 5, then high frequency resolutions patterns are extracted from high kVp projections and added to acquired low kVp projections, according to embodiments of the invention. According to one embodiment, as illustrated in FIG. 6, low kVp signal resolution is enhanced or mitigated by using neighboring high kVp projection data. In this embodiment, channels of low kVp projections are assessed against an LST and, if one or more channels is below the LST, then adjacent high kVp projections are combined and a high frequency component is extracted therefrom. In one embodiment, the LST is defined as a point wherein low signal corruption begins, and may be empirically determined relative to a basis phantom and based on operating conditions. For instance, the LST may be determined based on one or more parameters such as a number of views per rotation, focal spot wobble, gantry rotation period, geometric efficiency, component geometry (i.e., source, detector, etc.), detector light output, DAS efficiency, DAS electronic noise, kVp, mA, or the like.

Thus, FIG. 6 represents a loop 300 for low kVp data mitigation that begins at step 302, where a low kVp projection is identified for possible mitigation. At step 304, channels of the identified low kVp projection are assessed against an LST. If not below the LST 306, then a query is made at step 308 as to whether more low kVp datasets should be assessed. If so 310, then the next low kVp projection dataset is considered at step 312. However, if all low kVp projections have been assessed and there are none remaining for consideration 314, then an image is reconstructed using high kVp data and the mitigated low kVp data at step 316 as discussed with respect to FIG. 5 at step 214.

Low kVp data may be mitigated as further illustrated in FIG. 6. Thus, when assessing low kVp projection data against the LST, as stated, if one or more channels of the low kVp dataset is below the LST 318, then the low kVp projection dataset is corrected, using high frequency data extracted from the high kVp projection data H(n), according to an embodiment of the invention.

Thus, according to this embodiment, H(n-1) and H(n+1) are determined at step 320 that are adjacent to the low kVp projection data L(n) that is to be mitigated. An average or weighted average high kVp projection $H_a(n)$ is determined at step 322 using:

$$H_a(n)=(H(n-1)+H(n+1))/2; \qquad \text{Eqn. 1.}$$

A scaled high kVp projection, $H_s(n)$ is determined at step 324 using the average or weighted average high kVp projection $H_a(n)$:

$$H_s(n)=(1-H_a(n))*Sf(n)+1; \qquad \text{Eqn. 2.}$$

The invention applies to averaging of data, whether the averaging is simple averaging or by weighted averaging. Averaging typically includes simple averaging of data, whereas a weighted average includes averaging data with non-equal weighting, as is understood in the art. In other words, as is understood in the art, some data may be weighted more than others. However and regardless, both weighted and non-weighted averaging are included within embodiments of the invention and are encompassed when referring to any type of averaging.

Scaling factor Sf(n) may be determined by a variety of methods, and will be further illustrated below, according to embodiments of the invention. A filtered high kVp projection $H_{sm}(n)$ is formed at step 326 by filtering out high frequency components from the scaled high kVp projection, $H_s(n)$. High frequencies are extracted at step 328 from the scaled high kVp projection, $H_s(n)$ by subtracting the filtered high kVp projection $H_{sm}(n)$ therefrom, to form a high frequency projection $H_\delta(n)$:

$$H_\delta(n)=H_s(n)-H_{sm}(n); \qquad \text{Eqn. 3.}$$

Filtered or base low kVp projection data $L_m(n)$ is formed at step 330 by filtering out high frequency components from the low kVp projection data L(n). Once filtered, high frequency data $H_\delta(n)$ is added to the filtered low kVp projection $L_m(n)$ to form a low kVp projection for reconstruction, $L_R(n)$, at step 332:

$$L_R(n)=L_m(n)+H_\delta(n); \qquad \text{Eqn. 4.}$$

Scaling factor Sf(n) may be determined by a variety of methods. According to one embodiment, an average or weighted average scaling factor Sf(n) is determined by using both a mean low kVp projection, $L_M(n)$, as determined from the low kVp projection L(n), and the averaged or weighted average high kVp projection, $H_a(n)$ (as determined above):

$$Sf(n) = \frac{\Sigma 1 - L_M(n)}{\Sigma 1 - H_a(a)}; \qquad \text{Eqn. 5.}$$

Figure 7:
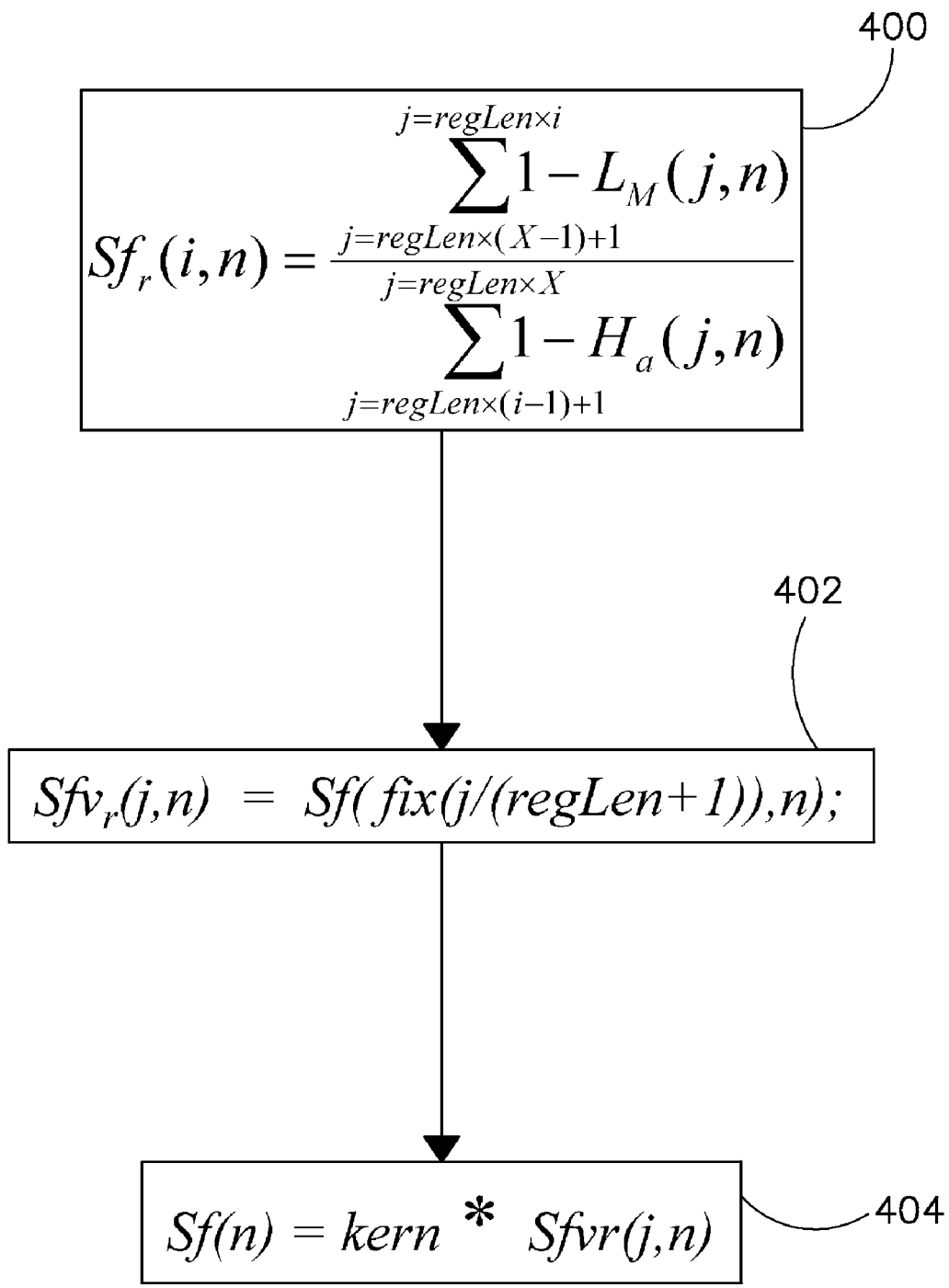
FIG. 7 is a flowchart for determining local region projection scaling according to an embodiment of the invention.

According to another embodiment, scaling factor Sf(n) is determined over a local bin or sub-region. According to this embodiment, a method of determining scaling factor Sf(n) includes calculating a local scale factor for regions of channel bins (for example 75 wide), and creating a channel dependent scale factor vector and low pass filtering the scale factor vector (for example with a 150 point wide hanning kernel). The example is based on a 71 channel single dimensional low pass signal correction filter. Thus, referring to FIG. 7, at step 400 a local region scaling factor $Sf_r$ is determined for regions of channel bins, a channel dependent scale factor having constant values is created in accordance with $Sf_r(j,n)$ within each sub-region bin at step 402, and the scale factor is low pass filtered at step 404 using, for instance, a 50 point hanning kernel.

Figure 8:
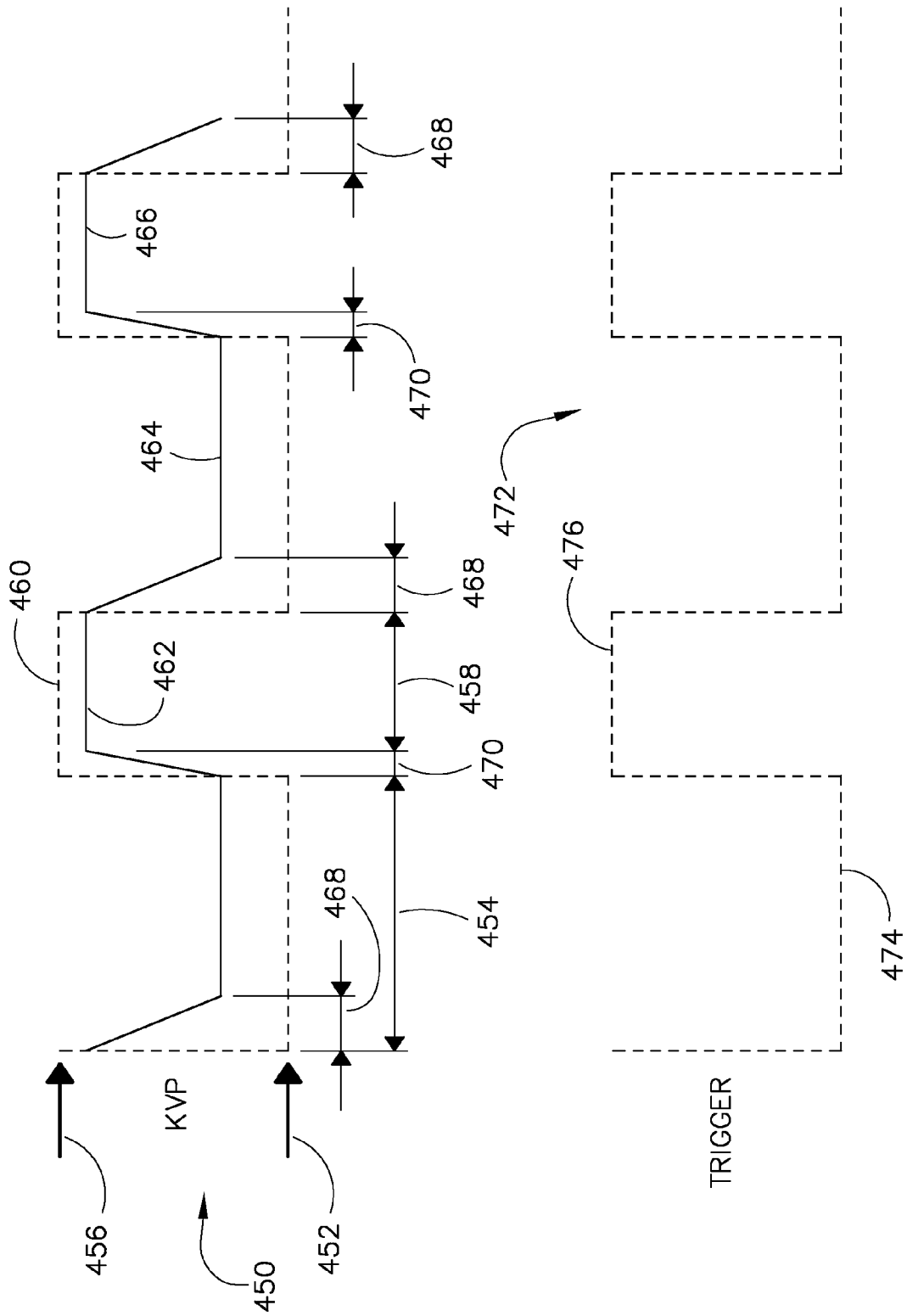
FIG. 8 is an illustration of obtaining low kVp and high kVp projection data according to an embodiment of the invention.

In order to further minimize or mitigate the effects of low signal in low kVp CT imaging data, high and low kVp projection data may be obtained in such a fashion that may reduce the need to mitigate the acquired data using either a conventional or known low signal mitigation scheme, or by using a scheme such as is illustrated in FIG. 5 above. According to one method, high and low kVp projection data may be acquired in asymmetric sampling intervals such that the low kVp integration period is greater than the high kVp integration period. Thus, referring to FIG. 8, a generator, such as generator 29 of FIGS. 1 and 2, may be configured to output low and high kVp 450. Low kVp 452 is output for a first period 454, and high kVp 456 is output for a second period 458. As illustrated, first period 454 occurs for a time period that is greater than second time period 458. Also as illustrated, kVp set profile 460 illustrates set points or generator output voltages, and an actual or achieved kVp output 462 is illustrated which shows a resulting low kVp 464 that is typically greater than the output low kVp 452. Likewise, a resulting high kVp 466 is typically less than the output high kVp 456. Actual or achieved kVp output 462 includes resulting fall times 468 and rise times 470 due to the capacitance of the system and other known effects.

Correspondingly, low and high kVp integration 472 includes low kVp integration periods 474 and high kVp integration periods 476, which are caused to trigger in conjunction with switching from low kVp to high kVp, and vice versa. As such, integration of the low kVp signal occurs for a time period that is greater than a time period of integration of the high kVp signal. This allows more x-ray photons to be captured and integrated per sample, thereby increasing the desired detected signal above, for instance, electronic noise. In one embodiment, improvement may be realized by asymmetrically combining fixed trigger intervals. In one example, data may be sequentially acquired during three fixed sample intervals at low kVp and then sequentially during two fixed sample intervals at high kVp.

Thus, when data is acquired having asymmetric time intervals or with multiple/sequential low kVp shots and subsequently multiple/sequential high kVp shots, then embodiments of the invention include weighting the acquired projection data to account for the corresponding locations of the gantry, as understood in the art. For instance, when determining neighboring high kVp projection data at step 320, and subsequently averaging the acquired data as described with respect to Eqn. 1 above, then Eqn. 1 is appropriately modified by weighting the neighboring high kVp projections H(n−1) and H(n+1) to account for the asymmetry of the acquired data. Further, one skilled in the art will recognize that multiple neighboring high kVp projections may be used to obtain the average or weighted average high kVp projection $H_a(n)$ at step 322.

Yet another method that can be used independently or in conjunction with any of the disclosed methods and techniques herein is to increase the low kVp integration interval by decreasing the number of projections. This can be done while taking into account and optimizing for azimuthal resolution loss and view aliasing.

Further, it is possible to determine from scout data when projections are likely to be compromised. In one embodiment, orthogonal scan projection data is acquired for both lateral and anterior-posterior (AP) scout scans. After accounting for bowtie attenuation, for each Z-width covered per rotation, view averages may be obtained and separated into center and edge zones. A projection measure (PM) (attenuation in terms normalized to water) is compared to a low signal threshold (LST) that is a function of operating conditions for the scanner. In embodiments of the invention, patient attenuation and LST can be stated directly in terms of pre-log signal intensity or by using post log PM and LST. Accordingly, using both the lateral and the AP scout scans, and LST-PM can be determined for respective lateral and AP views and, if a LST-PM is below a set limit, then a reduced view rate in corresponding sections or views may be used.

In the above discussion, it should be understood that "low kVp" data is a general terminology to describe the projection dataset having worse statistics during a dual energy acquisition. For example, in a dual tube-detector configuration (two sets of tube-detector pairs that are offset by roughly 90-degree angle, as an example), additional filtration can be applied to the high kVp tube-detector (e.g., additional Sn filter for 140 kVp setting) and increased low kVp for the other tube-detector pair (e.g., increase from 80 kVp to 100 kVp). However, as stated, it is possible that the dataset with lower kVp setting (100 kVp) has lower noise than the higher kVp setting (140 kVp). In this case, the correction approach outlined above is applied to the higher kVp setting (140 kVp) instead of the lower kVp setting (100 kVp).

It should also be understood that the process outlined above (low-pass filtering of the "low kVp" data and addition of the high-pass filtered "high kVp" data) is for illustration purpose to demonstrate the leverage of "high kVp" information to correct for "low kVp" deficiencies. However, other approaches can be used to correct for such deficiencies, according to the invention. For example, for "low kVp" channels that exhibit significant noise, we could fit corresponding "high kVp" channels to "low kVp" channels to obtain an estimation of erroneous "low kVp" channels. To be more specific, if a channel k of the "low kVp" channel does not pass a threshold test, nearby channels from k−n to k+n of the "high kVp" data may be used to perform a polynomial fit of the "low kVp" data from k−n to k+n to obtain an estimation of "low kVp" channel k with a fitted "high kVp" channel k.

It should also be understood that filtration parameters (e.g., both high-pass and low-pass described in FIG. 6) can be changed dynamically dependent on measured projection data.

Figure 9:
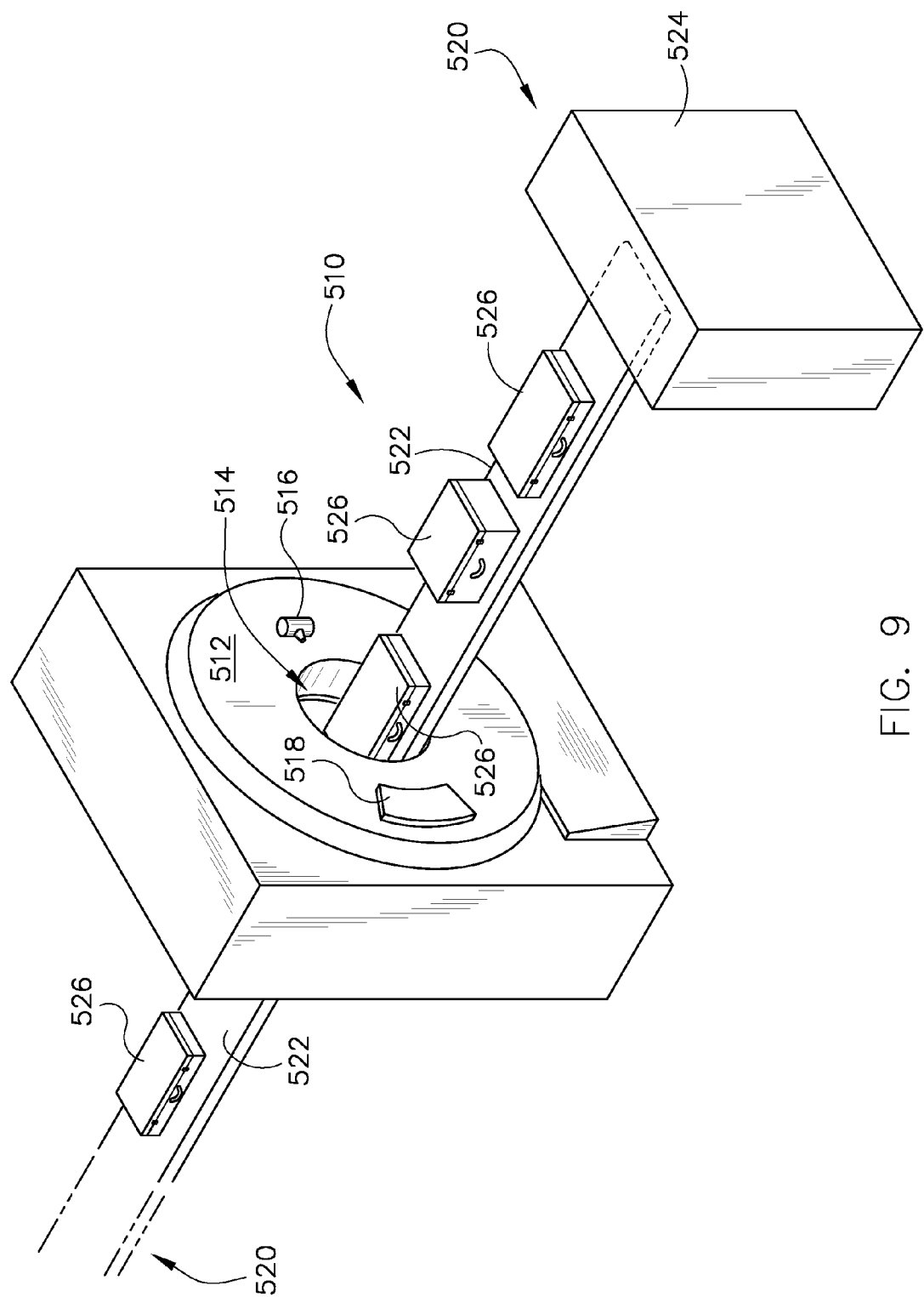
FIG. 9 is a pictorial view of a CT system for use with a non-invasive package inspection system according to an embodiment of the invention.

Referring now to FIG. 9, package/baggage inspection system 510 includes a rotatable gantry 512 having an opening 514 therein through which packages or pieces of baggage may pass. The rotatable gantry 512 houses a high frequency electromagnetic energy source 516 as well as a detector assembly 518 having scintillator arrays comprised of scintillator cells similar to that shown in FIG. 4. A conveyor system 520 also is provided and includes a conveyor belt 522 supported by structure 524 to automatically and continuously pass packages or baggage pieces 526 through opening 514 to be scanned. Objects 526 are fed through opening 514 by conveyor belt 522, imaging data is then acquired, and the conveyor belt 522 removes the packages 526 from opening 514 in a controlled and continuous manner. As a result, postal inspectors, baggage handlers, and other security personnel may non-invasively inspect the contents of packages 526 for explosives, knives, guns, contraband, etc.

An implementation of embodiments of the invention in an example comprises a plurality of components such as one or more of electronic components, hardware components, and/or computer software components. A number of such components can be combined or divided in an implementation of the embodiments of the invention. An exemplary component of an implementation of the embodiments of the invention employs and/or comprises a set and/or series of computer instructions written in or implemented with any of a number of programming languages, as will be appreciated by those skilled in the art.

An implementation of the embodiments of the invention in an example employs one or more computer readable storage media. An example of a computer-readable signal-bearing medium for an implementation of the embodiments of the invention comprises the recordable data storage medium of the image reconstructor 34, and/or the mass storage device 38 of the computer 36. A computer-readable storage medium for an implementation of the embodiments of the invention in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory.

A technical contribution for the disclosed method and apparatus is that it provides for a computer-implemented apparatus and method of acquiring imaging data at more than one energy range using a multi-energy imaging source.

According to an embodiment of the invention, a CT system includes a rotatable gantry having an opening for receiving an object to be scanned, and a controller configured to obtain kVp projection data at a first kVp, obtain kVp projection data at a second kVp, extract data from the kVp projection data obtained at the second kVp, add the extracted data to the kVp projection data obtained at the first kVp to generate mitigated projection data at the first kVp, and generate an image using the mitigated projection data at the first kVp and using the projection data obtained at the second kVp.

According to another embodiment of the invention, a method of CT imaging includes obtaining one or more first kVp projection datasets, obtaining a plurality of second kVp projection datasets, extracting information from the plurality of second kVp projection datasets, adding the extracted information to one of the first kVp projection datasets to generate a corrected first kVp projection dataset, and generating an image using at least the corrected first kVp projection dataset.

According to yet another embodiment of the invention, a computer readable storage medium having stored thereon a computer program comprising instructions which when executed by a computer cause the computer to obtain first kVp view data, obtain second kVp view data, extract high frequency data from the second kVp view data, adjust the first kVp view data using the extracted high frequency data to generate adjusted first kVp view data, and generate an image using the adjusted first kVp view data.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Furthermore, while single energy and dual-energy techniques are discussed above, the invention encompasses approaches with more than two energies. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A CT system comprising:
    a rotatable gantry having an opening for receiving an object to be scanned; and
    a controller configured to:
        obtain kVp projection data at a first kVp;
        obtain kVp projection data at a second kVp;
        extract data from the kVp projection data obtained at the second kVp;
        add the extracted data to the kVp projection data obtained at the first kVp to generate mitigated projection data at the first kVp; and
        generate an image using the mitigated projection data at the first kVp and using the projection data obtained at the second kVp.

2. The CT system of claim 1 wherein the data extracted is one of high frequency data and statistical data.

3. The CT system of claim 1 comprising an x-ray source coupled to the gantry and configured to project x-rays through the opening and toward the object at a first kVp to generate the kVp projection data obtained at the first kVp, and configured to project x-rays through the opening and toward the object at a second kVp to generate the kVp projection data obtained at the second kVp.

4. The CT system of claim 1 wherein the first kVp is at a voltage that is lower than the second kVp.

5. The CT system of claim 1 wherein the controller is further configured to extract data from the projection data obtained at the first kVp to generate filtered kVp base projection data; and
    wherein the controller, in being configured to add extracted data to the kVp projection data obtained at the first kVp, is configured to add the extracted data to the filtered kVp base projection dataset.

6. The CT system of claim 1 wherein the controller, in being configured to extract the data, is configured to:
    average projection data obtained at the second kVp to generate averaged second kVp projection data;
    multiply the averaged second kVp projection data by a scale factor function to generate a scaled projection; and
    subtract the scaled projection from the averaged second kVp projection data to generate the extracted data.

7. The CT system of claim 6 wherein the controller is configured to multiply the projection data obtained at the first kVp by the scale factor function.

8. The CT system of claim 6 wherein the scale factor function is a function of at least the averaged second kVp projection data and the kVp projection data obtained at the first kVp.

9. The CT system of claim 1 wherein the kVp projection data obtained at the first kVp is obtained during a sampling period that is greater than a sampling period of projection data obtained at the second kVp.

10. The CT system of claim 1 wherein the projection data obtained at the first kVp is obtained during a first number of views, and the projection data obtained at the second kVp is obtained during a second number of views, wherein the second number of views is less than the first number of views.

11. A method of CT imaging comprising:
    obtaining one or more first kVp projection datasets;
    obtaining a plurality of second kVp projection datasets;
    extracting information from the plurality of second kVp projection datasets;
    adding the extracted information to one of the first kVp projection datasets to generate a corrected first kVp projection dataset; and
    generating an image using at least the corrected first kVp projection dataset.

12. The method of claim 11 wherein the steps of extracting information and adding the extracted information comprise extracting a high frequency component from the plurality of second kVp projection datasets, and adding the high frequency component to the one or more first kVp projection datasets.

13. The method of claim 11 wherein obtaining the plurality of second kVp projection datasets includes obtaining the plurality of second kVp projection datasets at a voltage level that is greater than a voltage level of the obtained one or more first kVp projection datasets.

14. The method of claim 11 further comprising extracting information from at least one of the first kVp projection datasets to generate a first kVp filtered dataset, wherein the step of adding the extracted information to one of the first kVp projection datasets comprises adding the extracted information to the first kVp filtered dataset.

15. The method of claim 11 further comprising averaging two or more of the plurality of second kVp projection datasets to form an averaged second kVp projection dataset, wherein the step of extracting the information comprises extracting the information from the averaged second kVp projection dataset.

16. The method of claim 15 wherein averaging comprises using a second kVp projection obtained prior to obtaining the one or more first kVp projection datasets and using a second kVp projection obtained subsequent to one or more first kVp projection datasets.

17. The method of claim 11 wherein the step of generating the image further comprises using the one or more second kVp projection datasets.

18. The method of claim 11 wherein the steps of obtaining the one or more first kVp projection datasets and obtaining the one or more second kVp projection datasets comprise obtaining, in sequence, a single first kVp dataset, a single second kVp dataset, and a single first kVp dataset.

19. The method of claim 11 wherein the steps of obtaining the one or more first kVp projection datasets and obtaining the one or more second kVp projection datasets comprise obtaining two or more first kVp datasets in sequence, and obtaining two more second kVp datasets in sequence.

20. The method of claim 19 wherein a greater number of first kVp datasets is obtained in sequence than a number of second kVp datasets.

21. A computer readable storage medium having stored thereon a computer program comprising instructions which when executed by a computer cause the computer to:
- obtain first kVp view data;
- obtain second kVp view data;
- extract high frequency data from the second kVp view data;
- adjust the first kVp view data using the extracted high frequency data to generate adjusted first kVp view data; and
- generate an image using the adjusted first kVp view data.

22. The computer readable storage medium of claim 21 wherein the computer is caused to obtain the first kVp view data and the second kVp view data from x-rays generated via a single x-ray source.

23. The computer readable storage medium of claim 21 wherein the computer is caused to generate the image using the obtained second kVp view data.

24. The computer readable storage medium of claim 21 wherein the computer is caused to obtain the first kVp view data at multiple sequential view locations and prior to energizing the x-ray source to a second kVp potential, and wherein the computer is caused to obtain the second kVp view data at multiple sequential view locations.

25. The computer readable storage medium of claim 21 wherein the computer is caused to:
- energize an x-ray source for a first time period at a first kVp potential while obtaining the first kVp view data; and
- energize the x-ray source, for a second time period that is shorter than the first time period, at a second kVp potential while obtaining the second kVp view data.

26. The computer readable storage medium of claim 21 wherein the computer is caused to obtain the second kVp view data by averaging view data acquired at the second kVp immediately prior to, and immediately subsequent to, acquiring the first kVp view data.

27. The computer readable storage medium of claim 26 wherein the computer is caused to extract the high frequency data from the averaged view data acquired at the second kVp.

* * * * *